United States Patent [19]
Davis et al.

[11] Patent Number: 5,882,194
[45] Date of Patent: Mar. 16, 1999

[54] ILLUMINATED SUCTION TOOL WITH A DISPOSABLE TIP

[76] Inventors: Warren Davis, 942 Eldorado La., Las Vegas, Nev. 89123; David Wasserman, 2095 Mohigan Way, Las Vegas, Nev. 89109; Robert Dybus, 1437 Rawhide Rd., Boulder City, Nev. 89005

[21] Appl. No.: 2,073

[22] Filed: Jan. 8, 1998

Related U.S. Application Data

[63] Continuation of Ser. No. 692,917, Jul. 31, 1996, abandoned, which is a continuation-in-part of Ser. No. 562,730, Nov. 27, 1995.

[51] Int. Cl.[6] .............................. A61C 1/00; A61C 17/06
[52] U.S. Cl. ................................. 433/29; 433/91; 433/95
[58] Field of Search ................................. 433/29, 31, 91, 433/93, 95, 96, 80; 604/119, 902; 600/191, 156, 138; 239/16, 24, 25, 33; 215/388

[56] References Cited

U.S. PATENT DOCUMENTS

| | | | |
|---|---|---|---|
| 3,453,735 | 7/1969 | Burt | 433/96 |
| 3,864,831 | 2/1975 | Drake | 433/91 |
| 4,022,218 | 5/1977 | Riddick | 604/902 |
| 4,204,328 | 5/1980 | Kutner | 433/29 |
| 4,878,900 | 11/1989 | Sundt | 433/91 |
| 5,295,826 | 3/1994 | Yandell et al. | 433/31 |

*Primary Examiner*—Cary E. O'Connor
*Attorney, Agent, or Firm*—John Edward Roethel

[57] ABSTRACT

A dental suction tool has a disposable sanitary plastic suction tip to prevent cross contamination from one patient to the next. Additionally, a light source such as a fiberoptic bundle with or without a ring light is provided on the interior of the dental suction tool to provide light to the end of the plastic disposable suction tip. Illumination from the ring light or directly from the fiberoptic bundle is transmitted along the length of the suction tip and is emitted from the end thereof to illuminate the oral cavity during dental procedures.

22 Claims, 19 Drawing Sheets

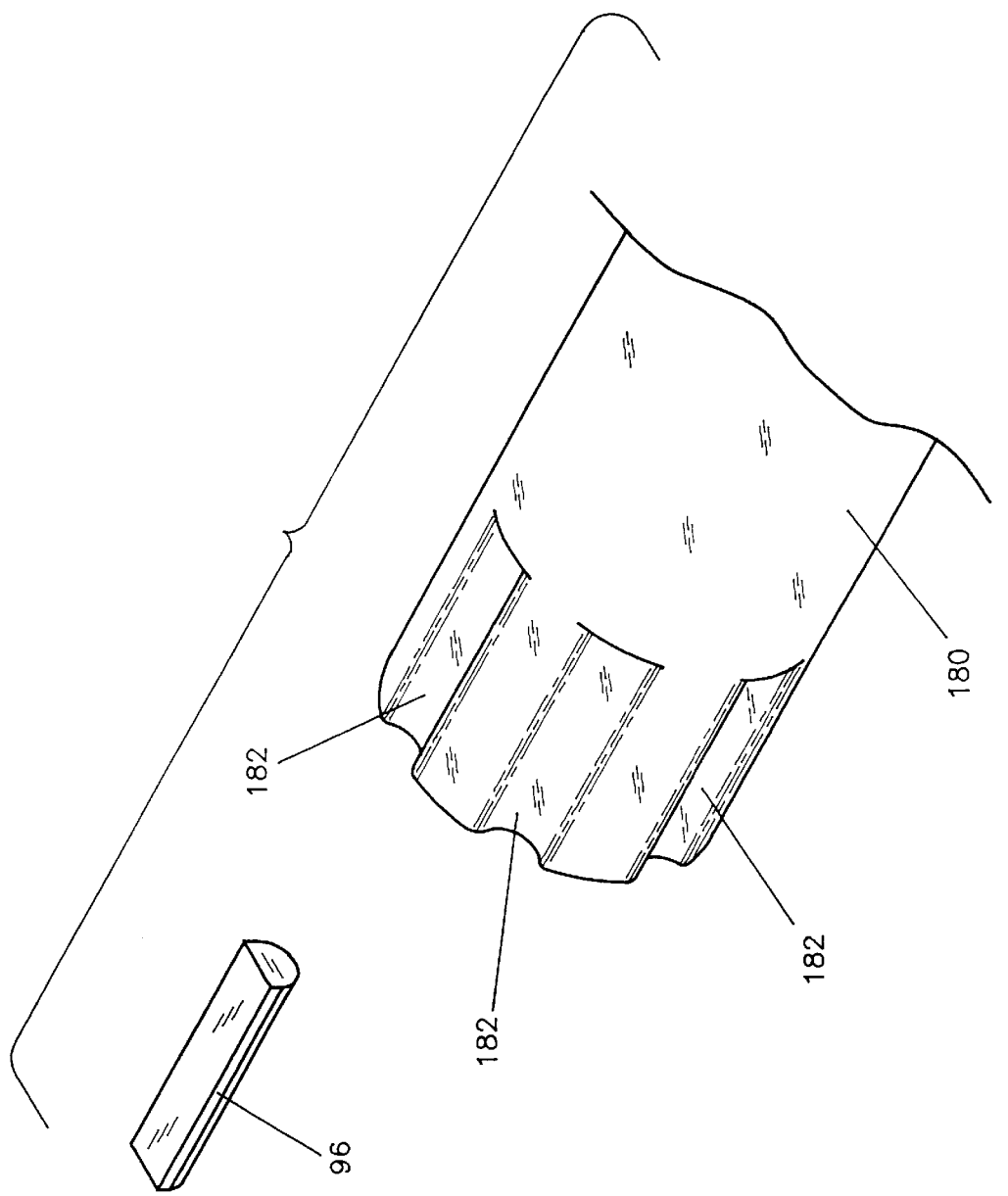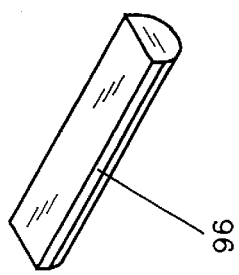
FIG-9

ILLUMINATED SUCTION TOOL WITH A DISPOSABLE TIP

CROSS-REFERENCE TO RELATED APPLICATION

This application is a continuation of application Ser. No. 08/692,917, filed Jul. 31, 1997, now abandoned, which is a continuation-in-part of application Ser. No. 08/562,730, filed Nov. 27, 1995, entitled "Illuminated Suction Tool with a Disposable Tip", now pending.

BACKGROUND OF THE INVENTION

This invention relates to a suction tool, and more particularly to suction tool with a disposable tip that also provides illumination to the oral cavity of the patient.

The present invention was developed to add further function to the widely accepted evacuation systems currently used for suction or aspiration. The concept of suction or aspiration in the dental office has its roots in the old fashioned spittoon. The spittoon was later replaced by the gravity flow cuspidor, then by the flush cup and finally by the suction tip/aspirator tip/vacuum tip which are interchangeable terms varying by the user and based on the size of the aperture in the device.

These dental suction instruments are used by dentists to remove fluids and other foreign objects that accrue in the patient's oral cavity during typical dental procedures. The conventional dental suction tool comprises a suction tip connected by a long tubing to a vacuum source. The dental suction tool can be configured to hang in the corner of the patient's mouth or is manipulated by the dentist to suction the oral cavity.

With the rising incidence of communicable diseases such as hepatitis and acquired immune deficiency syndrome, extreme care must be taken to prevent the transmission of germs (viral or bacteria) from one patient to the next. With the conventional suction devices, it is necessary to sterilize at least the tip of the suction device after each patient use. During the use of the suction device, water, saliva and blood from the patient's mouth is drawn into the tip for removal from the oral cavity. If cleaning and sterilization is not effected, it would be very easy to transfer infection from one patient to the next. Also, latent bacterial growth can be promoted in both the tip and the entire vacuum suction system lines because of the existence of this potentially contaminating material. To further mitigate this possibility of cross-contamination from one patient to the next, the routine sterilization of suction tips is desirable.

It is desirable to also supply light into the oral cavity to assist the dentist in performing necessary dental procedures. Most dental operatories have an overhead task lighting system with reflective surfaces that help concentrate the light on the patient's mouth. However, the dentist will often stand in the path of the light which minimizes the effectiveness of the overhead light. One of the major nuisances and frustrations in the practice of dentistry is the constant need for the dentist to spend time adjusting the direction of this overhead lighting.

Various dental tools have been provided with a light source to assist the dentist during various dental activities. For example, a typical dental drill will include a fiberoptic bundle that transmits light from a light source to the end of the dental drill which allows the dentist to provide light directly to the area in which the drilling is occurring. Representative of this technology are the disclosures shown in U.S. Pat. No. 4,507,085 (Mosimann) and U.S. Pat. No. 5,088,924 (Woodward).

Dental syringe tip handpieces have also been provided with a light source to illuminate the area into which the air and/or water are to be sprayed. Representative of these devices is the disclosure of U.S. Pat. No. 4,619,612 (Weber) which shows a fiberoptic bundle disposed down the center of a metal syringe tip assembly. A light bulb acts as the light source and is disposed in the interior of the handpiece. The syringe tip used in the disclosure of the Weber patent is a metal, non-disposable syringe tip which must be autoclaved prior to use on the next patient.

Previous attempts to use light in conjunction with a suction tip were done by running a fiberoptic bundle tangent and parallel to the suction tip. The optical conduit for the fiberoptic bundle was fixed to the suction tip by a series of clamps along the length of the suction tip. However, the results from this configuration were less than desirable for several reasons.

The fiberoptic bundles that were attached to the suction tips still needed to be sterilized before being used on the next patient. Fiberoptic bundles are not particularly amenable to the heat of sterilization and the expense and inconvenience of frequent replacement of these fiberoptic bundles can be prohibitive. It is also necessary to clean up the areas on the suction tip at which the clamps are attached and this can be quite cumbersome and time consuming. Another problem with this fiberoptic bundle configuration is that the light is positioned off-center from the suction tip so that the light being transmitted into the oral cavity of the patient still casts shadows from the suction tip, itself, which can do more harm than good.

The novel concept developed herein is to transmit light to the field of operation by transmitting a light source through a transparent plastic material which simultaneously serves as the suction tip of the dental suction device. The fact that the light is centered relative to the suction tip minimizes any shadows in the oral cavity and reduces the need for the dentist to rely on his overhead task lighting, which is constantly in need of adjustment.

It is proposed that the use of the present invention in conjunction with the light source that is coupled to the air/water syringe tip will provide sufficient light in the patient's oral cavity to obviate the need for the overhead task lighting and eliminate the time spent constantly adjusting this task lighting.

It is an object of the present invention to provide a disposable suction tip as part of the dental suction tool so that each patient can receive a clean and uncontaminated suction tip.

It is a feature of the present invention that the suction tip portion of a dental suction tool is made from a disposable plastic material.

It is an advantage of the present invention that cross-contamination between patients due to improperly cleaned or sterilized suction tips is eliminated because each patient is provided with a new, clean and uncontaminated suction tip that is only used on that patient.

It is a further object of the present invention to provide a useful source of light that can be transmitted into the oral cavity of the patient whenever the dentist is using a dental suction tool.

It is a further feature of the present invention to provide a light source at one end of the suction tip on the interior of the adaptor that holds the suction tip in the dental tool. Light from the light source is directed into one end of the suction tip and carried along the length thereof. At the opposite end of the suction tip, the light radiates from the suction tip and can be used to illuminate the oral cavity of the patient.

It is a further advantage of the present invention that a dentist will be able to illuminate the oral cavity using the same instrument that he is using to suction liquids and other foreign matter from the oral cavity of the patient. Any dental procedures that require use of the dental suction tool will be more easily, safely and effectively carried out because the dentist will be able to see exactly where in the oral cavity he is working.

Other objects, features and advantages of the present invention will become apparent from a consideration of the following detailed description.

SUMMARY OF THE INVENTION

A dental suction tool has a disposable sanitary plastic suction tip to prevent cross contamination from one patient to the next. Additionally, a light source such as a fiberoptic bundle with or without a ring light is provided on the interior of the dental suction tool to provide light to the end of the plastic disposable suction tip. Illumination from the ring light or directly from the fiberoptic bundle is transmitted along the length of the suction tip and is emitted from the end thereof to illuminate the oral cavity during dental procedures.

BRIEF DESCRIPTION OF THE DRAWINGS

FIG. 9 is an isometric exploded view of a modified suction tip and its corresponding key element of the present invention.

DETAILED DESCRIPTION OF THE PREFERRED EMBODIMENTS

Figure 1:
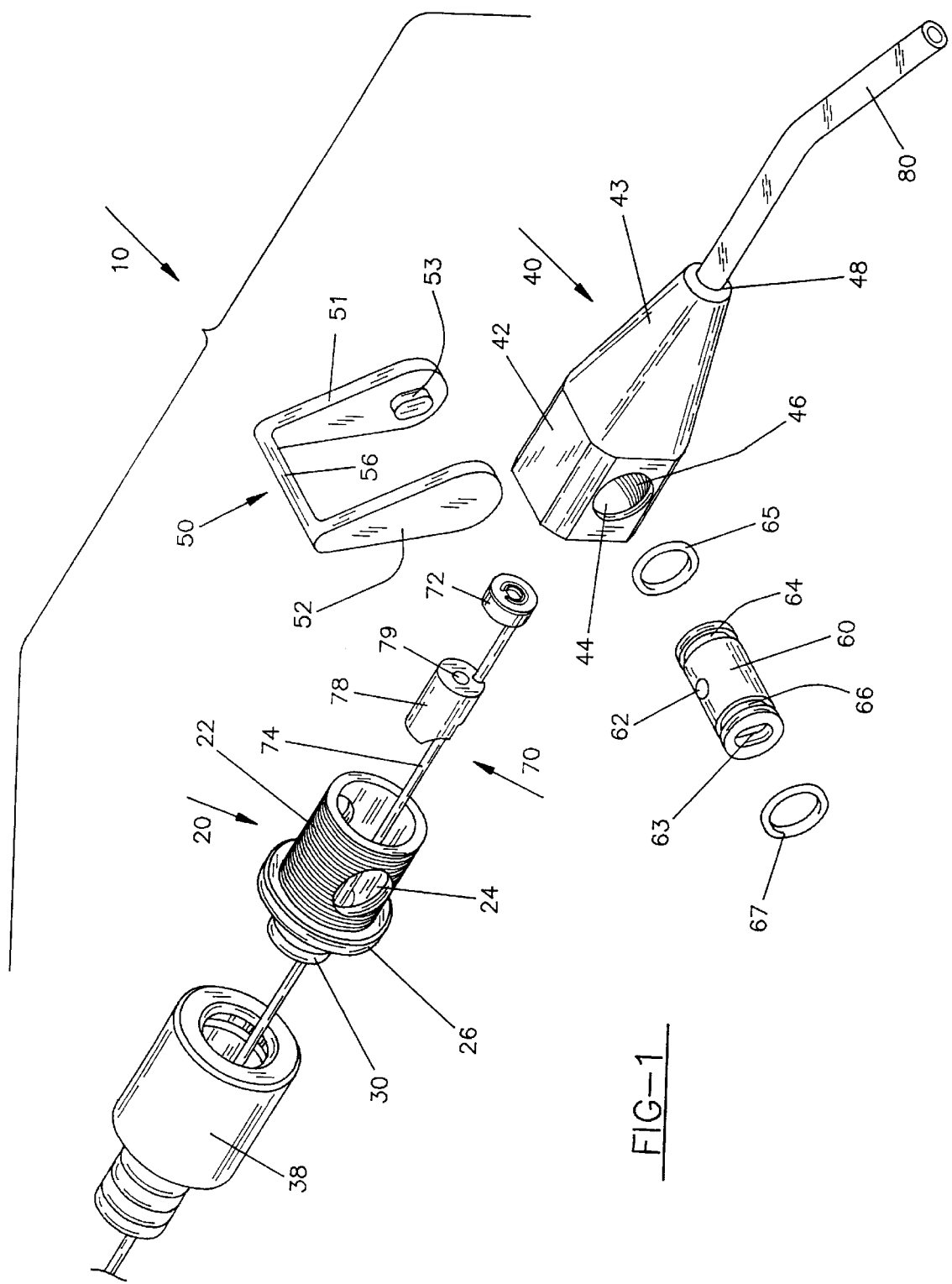
FIG. 1 shows an isometric exploded view of the dental suction tool of the present invention.

The dental suction tool of the present invention is shown generally at 10 in FIG. 1. The dental suction tool 10 comprises a valve cap 20, a valve body 40, a lever 50 and a light assembly 70. A suction tip 80 is mounted in the valve body 40 and the entire dental suction tool 10 is connected to a source of vacuum and electrical power (not shown).

The valve cap 20 comprises an externally threaded cap section 22, preferably configured as a hollow cylinder. On each of the diametrically opposite sides of the threaded cap section 22, a cylinder aperture 24 is provided of sufficient diameter to receive the rotating cylinder 60 therethrough when the dental suction tool 10 is assembled. Toward the rear of the threaded cap section 22, there is provided a cap top 26 and a cap extension 30. The cap extension 30 is provided with an annular groove 32 to receive the tubing connector base 38. The tubing connector base 38 is attached to the tubing (not shown) that runs from the power supply and the vacuum suction supply typically provided at a remote location from the dentist's chair.

The valve body 40 includes a generally hollow threaded body section 42 with a set of internal threads 46 that cooperate and receive the threaded cap section 22 of the valve cap 20 when the valve cap 20 is assembled with the valve body 40. The valve body 40 has a cylinder aperture 44 on its one side and another cylinder aperture (not shown) on the opposite side of the threaded body section 42. These cylinder apertures receive the rotating cylinder 60 when the dental suction tool 10 is assembled.

The rotating cylinder 60 is a generally cylindrical body with a cylinder passageway 62 diametrically therethrough. Each end of the rotating cylinder 60 has a fastening recess shaped to correspond to the fastening pins on the lever 50. One end of the rotating cylinder 60 has an annular groove 66 that receives an O ring 67 and the other end of the rotating cylinder 60 has a like annular groove 64 that receives an O ring 65.

The lever 50 can be of any suitable configuration such as the generally U-shaped configuration shown. The lever 50 has a first side arm 51 with a first fastening connector 53 mounted thereon that fits in the associated first fastening recess (not shown) on the rotating cylinder 60 and a second side arm 52 with a second fastening connector (not shown) that fits in the associated second fastening recess 63 on the rotating cylinder 60. Each of the first side arm 51 and the second side arm 52 are connected by the cross piece 56 so that each arm moves with the other to rotate the rotating cylinder 60 upon movement of the lever 50.

The dental suction tool 10 also includes a light assembly 70 comprising a light ring 72 at one end of a fiberoptic bundle 74 that extends the length of the dental suction tool 10. Adjacent, but slightly separated from the light ring 72 is an alignment cylinder 78 which assists in properly aligning the light assembly 70 on the interior of the dental suction tool 10 when all of the elements of the dental suction tool 10 are assembled together into its working state.

The valve body 40 includes a suction tip passageway 48 which opens at the end of the conical end section 43 in which is inserted the disposable suction tip 80. The suction tip 80 may have a number of configurations as will be further explained herein.

Figure 2:
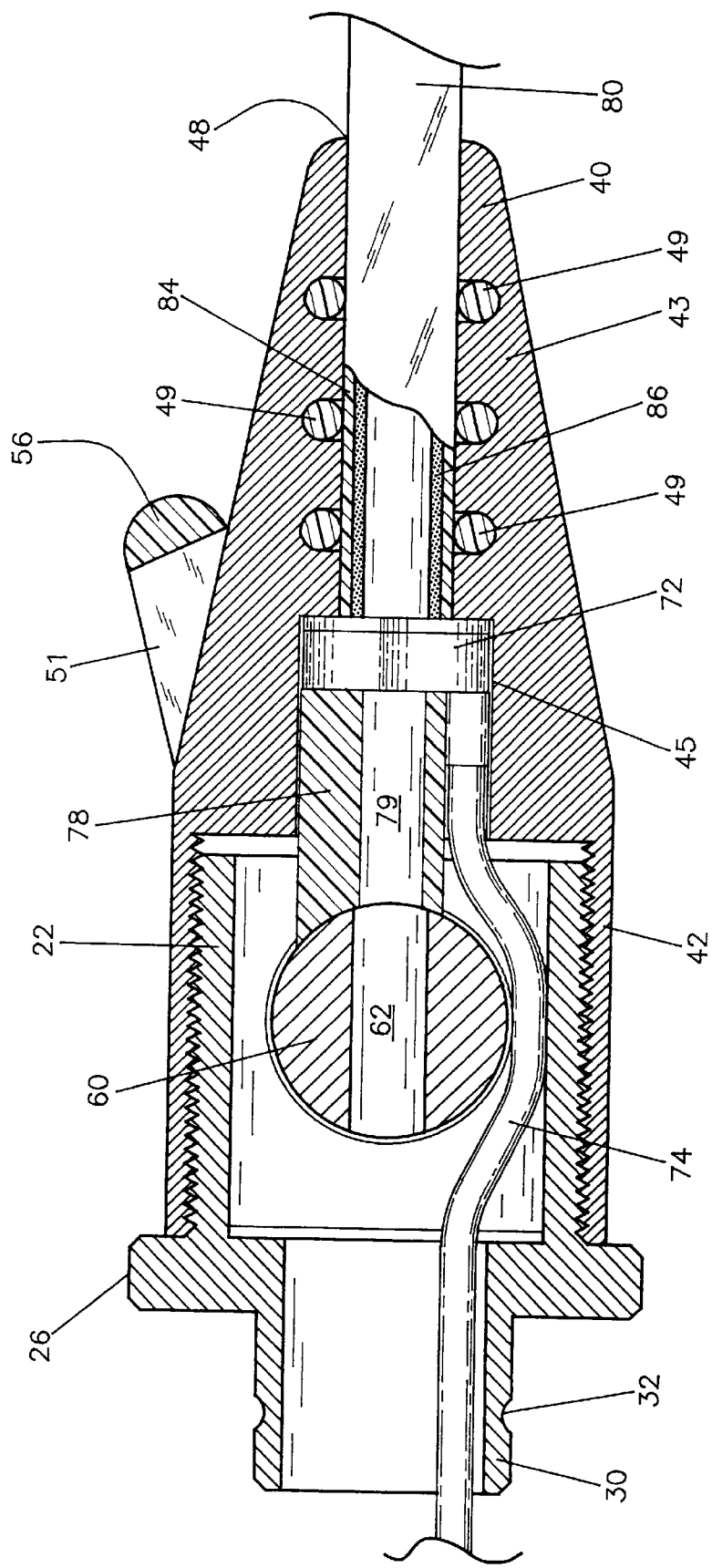
FIG. 2 is a cross sectional view of one embodiment of the dental suction tool of the present invention with the suction valve in the open position.

FIG. 2 shows in cross section the dental suction tool 10 in an assembled condition with the lever 50 set so that the rotating cylinder 60 is open to allow the vacuum source to provide suction to the suction tip 80. The valve body 40 has a light ring cavity 45 that receives the light ring 72 and the alignment cylinder 78. When the suction tip 80 is inserted into the suction tip passageway 48 of the valve body 40, the end of the suction tip 80 abuts the light ring 72. The suction tip 80 is held securely inside the valve body 40 by means of one or more O rings 49 provided therein along the length of the suction tip passageway 48. By simply pulling out the suction tip 80, a new suction tip 80 can be inserted into the valve body 40 for each new patient thereby maintaining a clean and sanitary suction tool and the elimination of any possible cross contamination between patients.

Activation of the power supply to the light assembly 70 transmits light through the fiberoptic bundle 74 and into the light ring 72. The light emitting from the light ring 72 is transmitted along the length of the suction tip 80 and out the end thereof into the patient's oral cavity.

In the embodiment of the invention shown in FIG. 2, the suction tip 80 is a bi-layered extrusion. The inner layer is a fiberoptic tubing 86 which will transmit the light from the light ring 72 along the length of the fiberoptic tubing 86 and out its end into the patient's mouth. The outer layer is plastic layer 84 which can be clear or opaque as desired. In the preferred embodiment, the plastic layer 84 should be a clear light-transmitting plastic material which can also transmit light from the light ring 72 along the length of the plastic layer 84.

Figure 3:
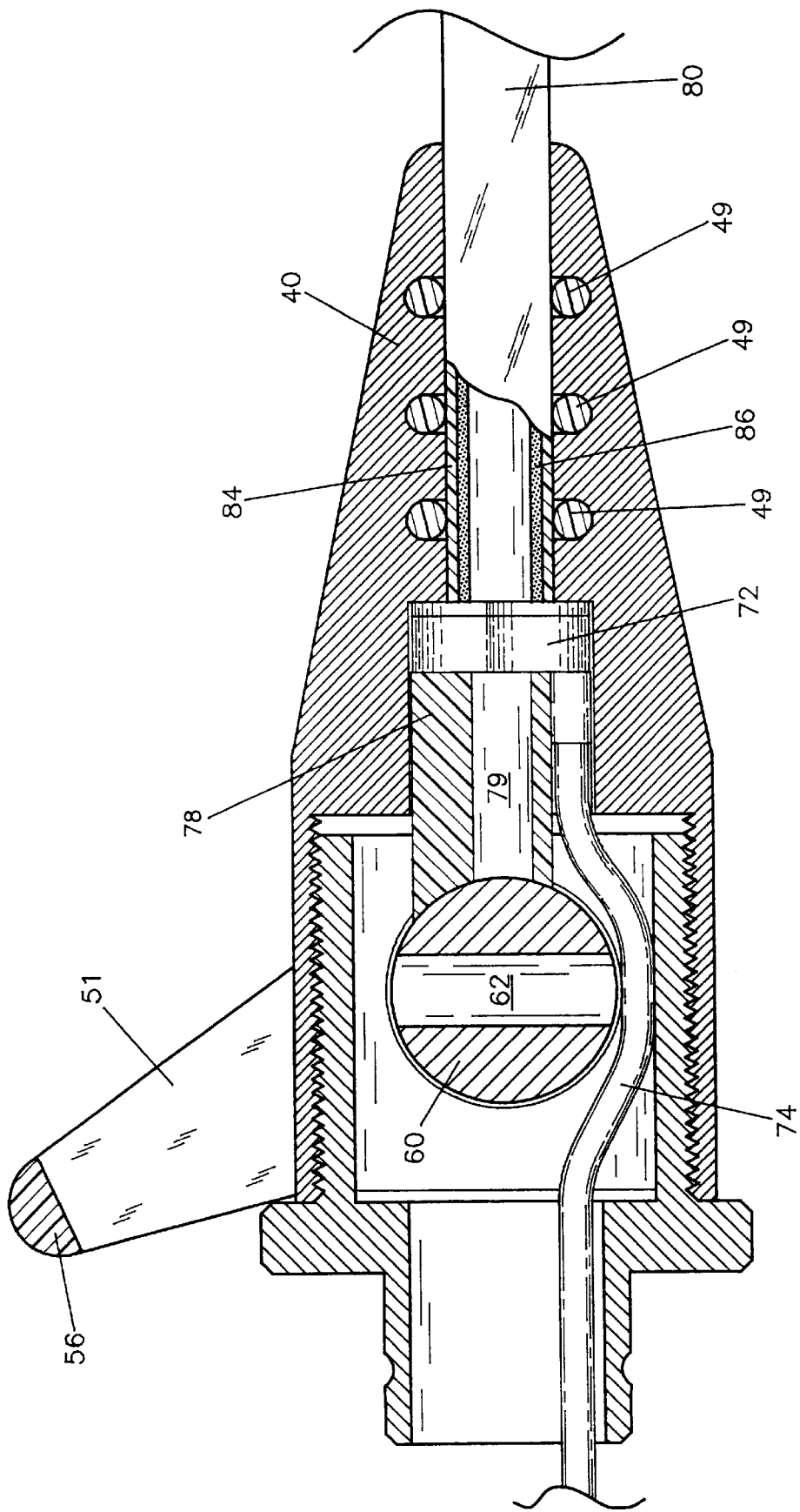
FIG. 3 is a cross sectional view of the dental suction tool of the present invention with the suction valve in the closed position.

When the lever 50 is rotated approximately 90° as shown in FIG. 3, the rotating cylinder 60 likewise rotates approximately 90°. This disassociates the cylinder passageway 62 from the alignment cylinder passageway 79 and no suction will be provided to the suction tip 80. However, light from the light ring 72 will continue to be transmitted along the length of the suction tip 80 and into the patient's oral cavity as long as power is supplied to the fiberoptic bundle 74. This allows the dental suction tool 10 to function as a light source even when suction is not required for a particular dental procedure.

Figure 4:
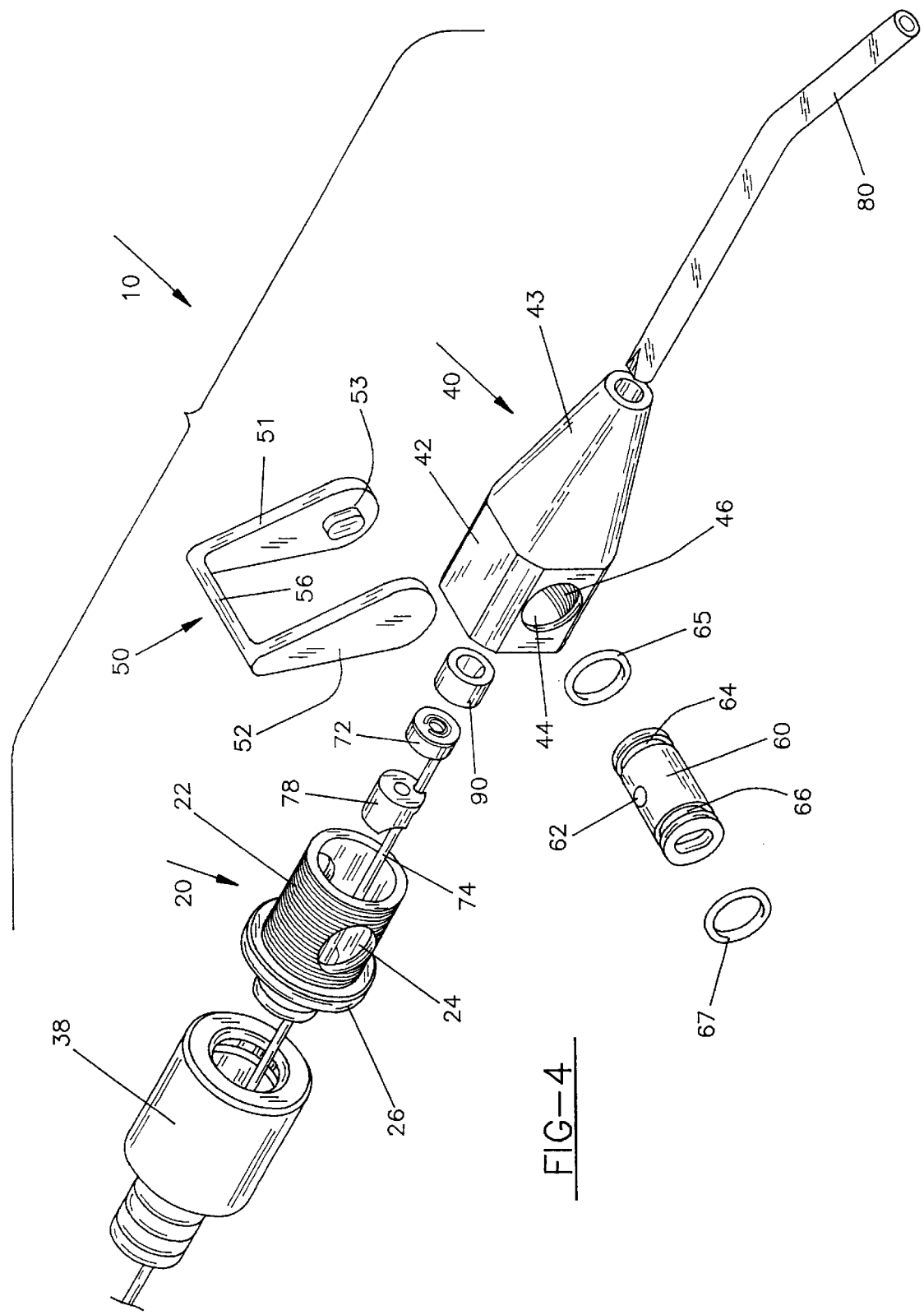
FIG. 4 shows an isometric exploded view of a modified dental suction tool of the present invention.
Figure 5:
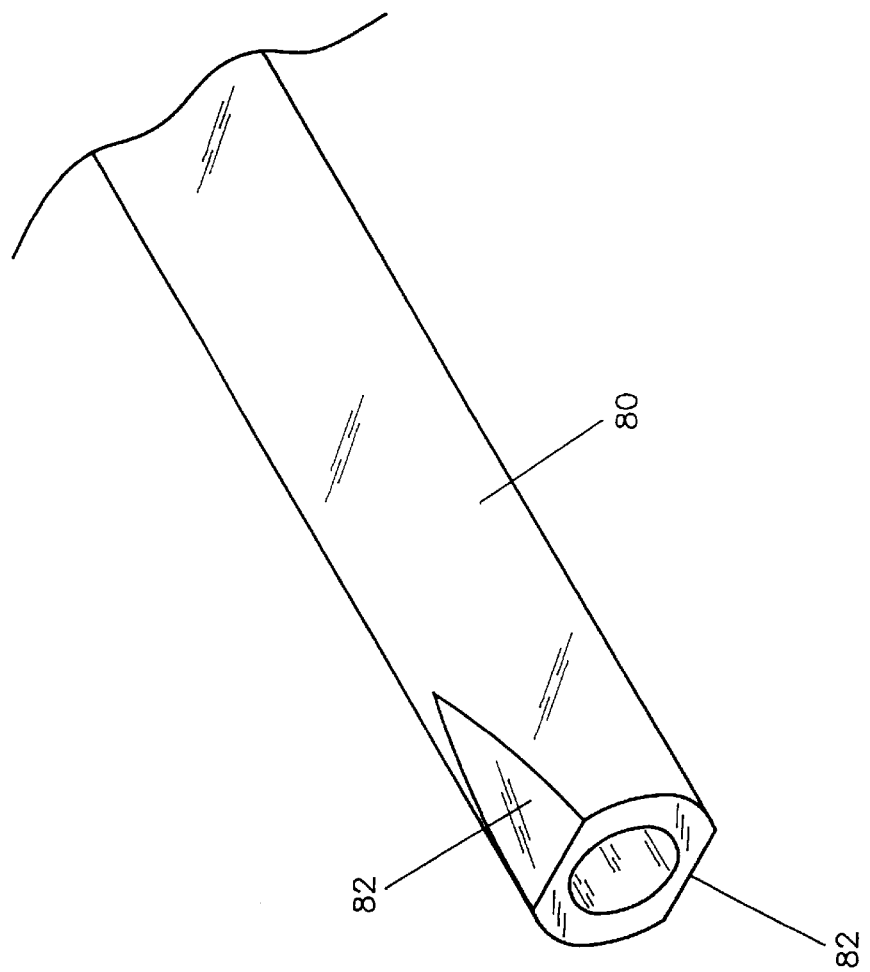
FIG. 5 shows an isometric view of a modified suction tip of the present invention.
Figure 6:
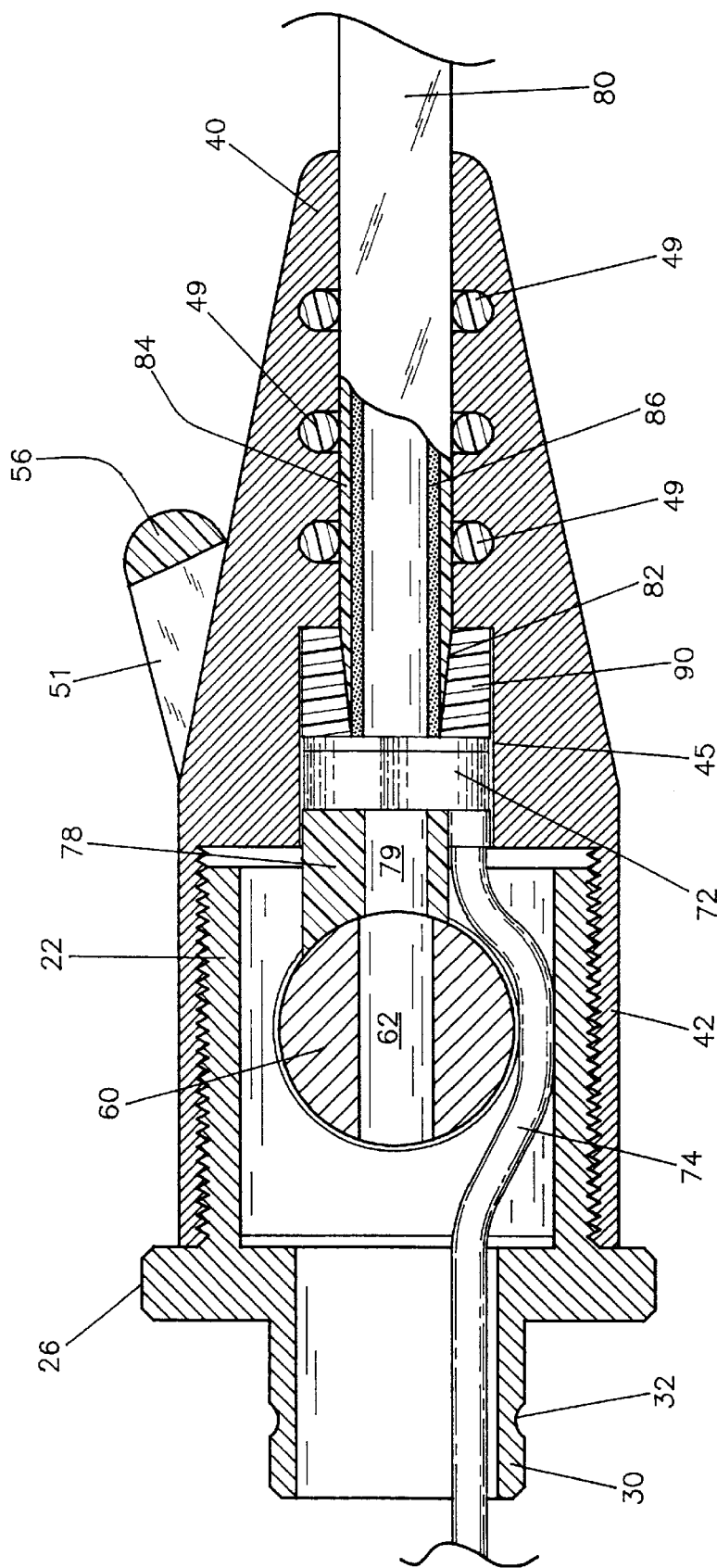
FIG. 6 is a cross sectional view of the modified dental suction tool shown in FIG. 4 with the suction valve in the open position.

FIGS. 4–6 show a modification of the dental suction tool 10 of the present invention. Like reference numerals are used to identify the elements from FIGS. 1–3 that are the same in FIGS. 4–6.

In FIGS. 4 and 6, a tip insertion block 90 is added to the rear cavity 45 in front of the light ring 72. As shown in FIGS. 5 and 6, the tip insertion block 90 has beveled top and bottom portions on its internal bore that correspond to the beveled sections 82 on diametrically opposed sides of the suction tip 80. As the suction tip 80 is inserted into the valve body 40, the beveled sections 82 align with the beveled top and bottom portions on the interior of the tip insertion block 90 and effect the proper alignment of the suction tip 80 in the valve body 40.

Figure 7:
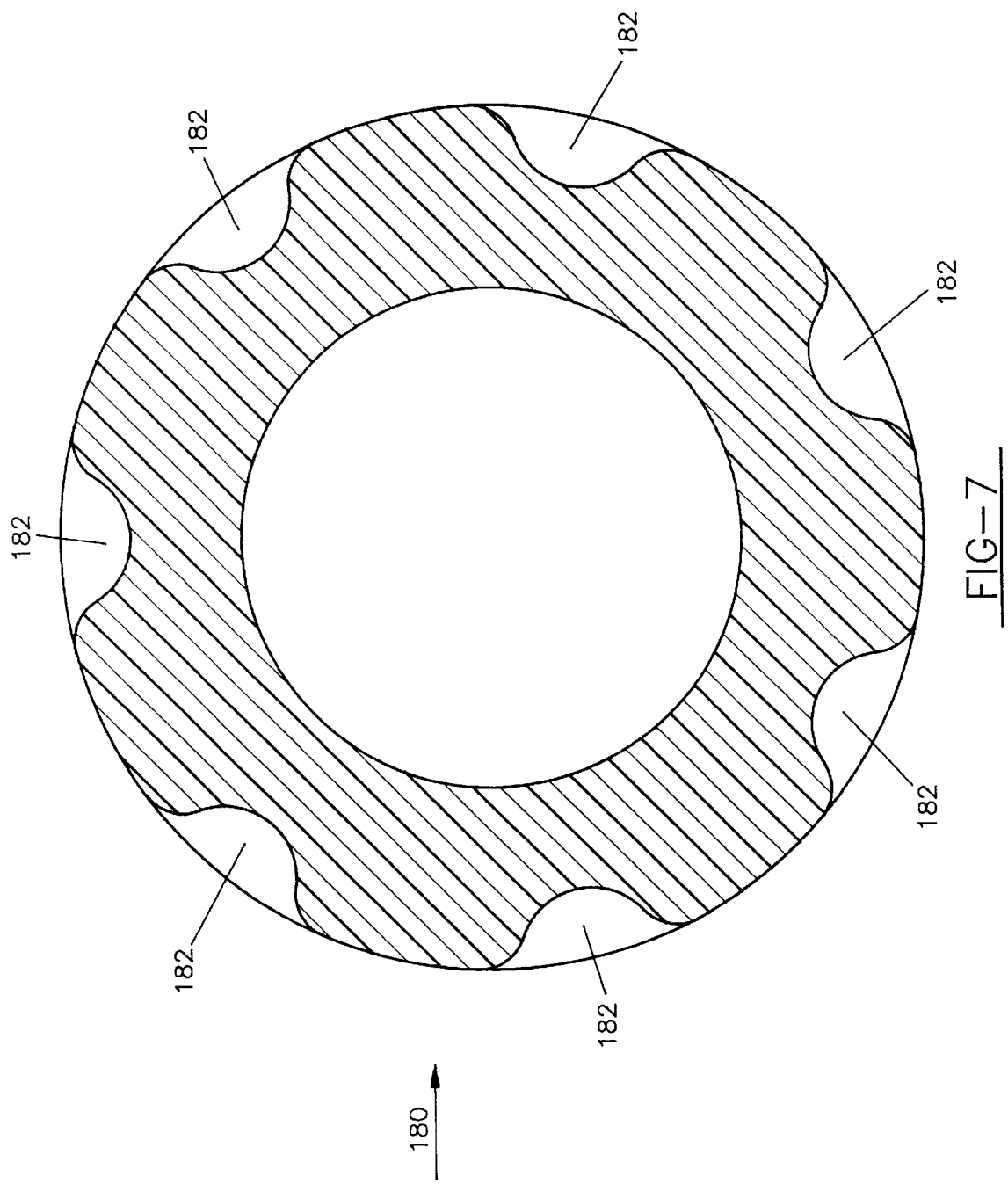
FIG. 7 shows an end view of another modified suction tip of the present invention.
Figure 8:
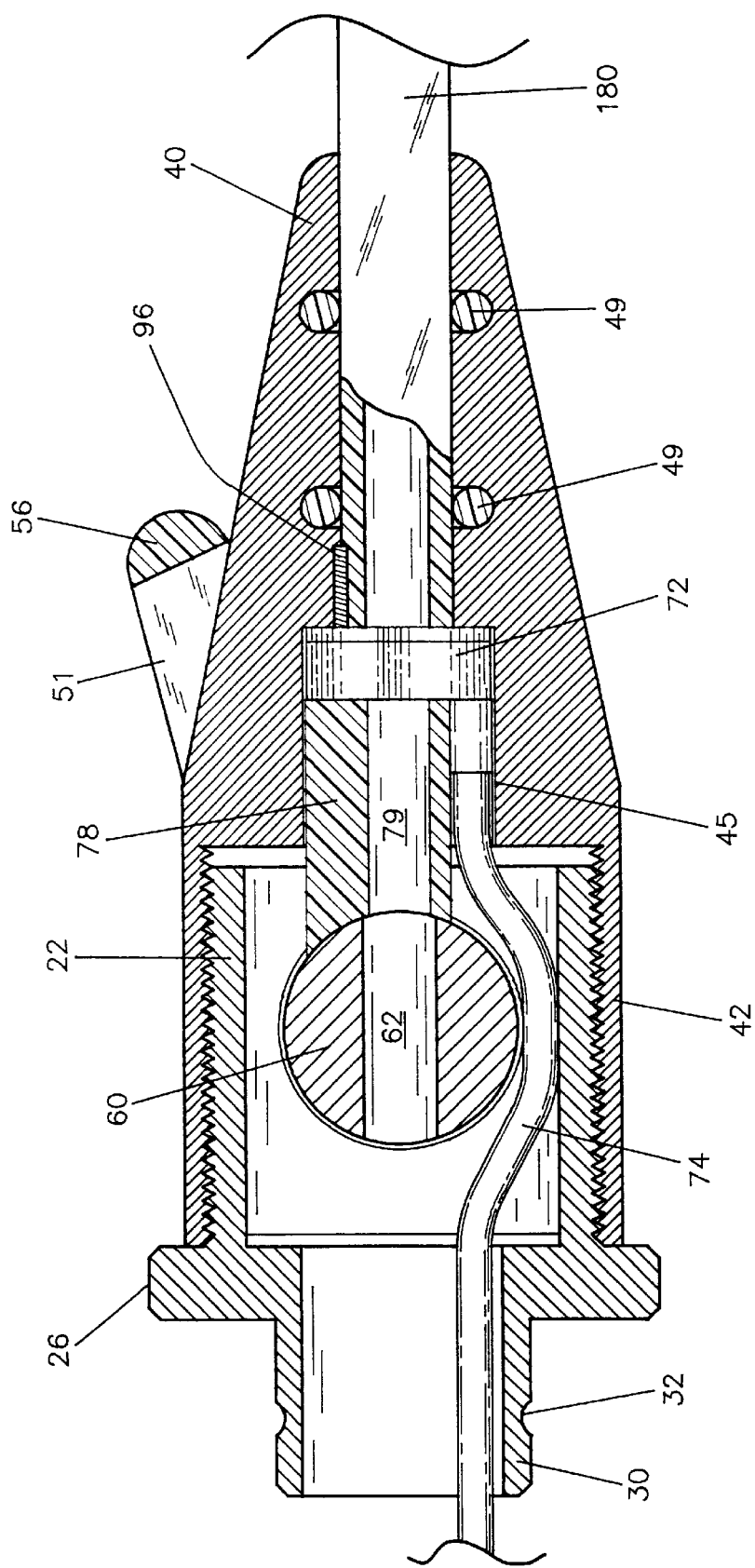
FIG. 8 is a cross sectional view of another modified dental suction tool with the suction valve in the open position.

FIGS. 7, 8 and 9 show another modification of the dental suction tool 10 of the present invention. Like reference numerals are used to identify the elements from FIGS. 1–3 that are the same in FIGS. 7 and 8.

In FIGS. 7, 8 and 9, a key 96 is added to the interior of the valve body 40 in front of the light ring 72. This key 96 will act as an alignment device when the suction tip 180 is inserted into the valve body 40.

As shown in FIGS. 7 and 9, the suction tip 180 has a plurality of recesses 182 that are positioned around the circumference of the suction tip 180 in equally spaced locations. When the suction tip 180 is inserted into the valve body 40, one of the recesses 182 aligns with the key 96 and effects the proper alignment of the suction tip 180 in the valve body 40. Since the suction tip 180 has a slight bend therein, by providing a plurality of recesses 182 around the circumference of the suction tip 180, a dentist may orient the suction tip 180 in a number of directions to permit the suction tip 180 to be utilized in any desired manner by the dentist.

FIG. 8 also shows another embodiment of the suction tip 180 which eliminates the fiberoptic layer on the inside of the suction tip. In this embodiment, a clear plastic material that is light transmitting is used for the suction tip 180. When the light ring 72 is activated, light emitting therefrom will travel through the body of the suction tip 180 and be emitted from the end thereof. This embodiment simplifies the manufacturing of the suction tip 180 and lowers its cost.

Figure 10:
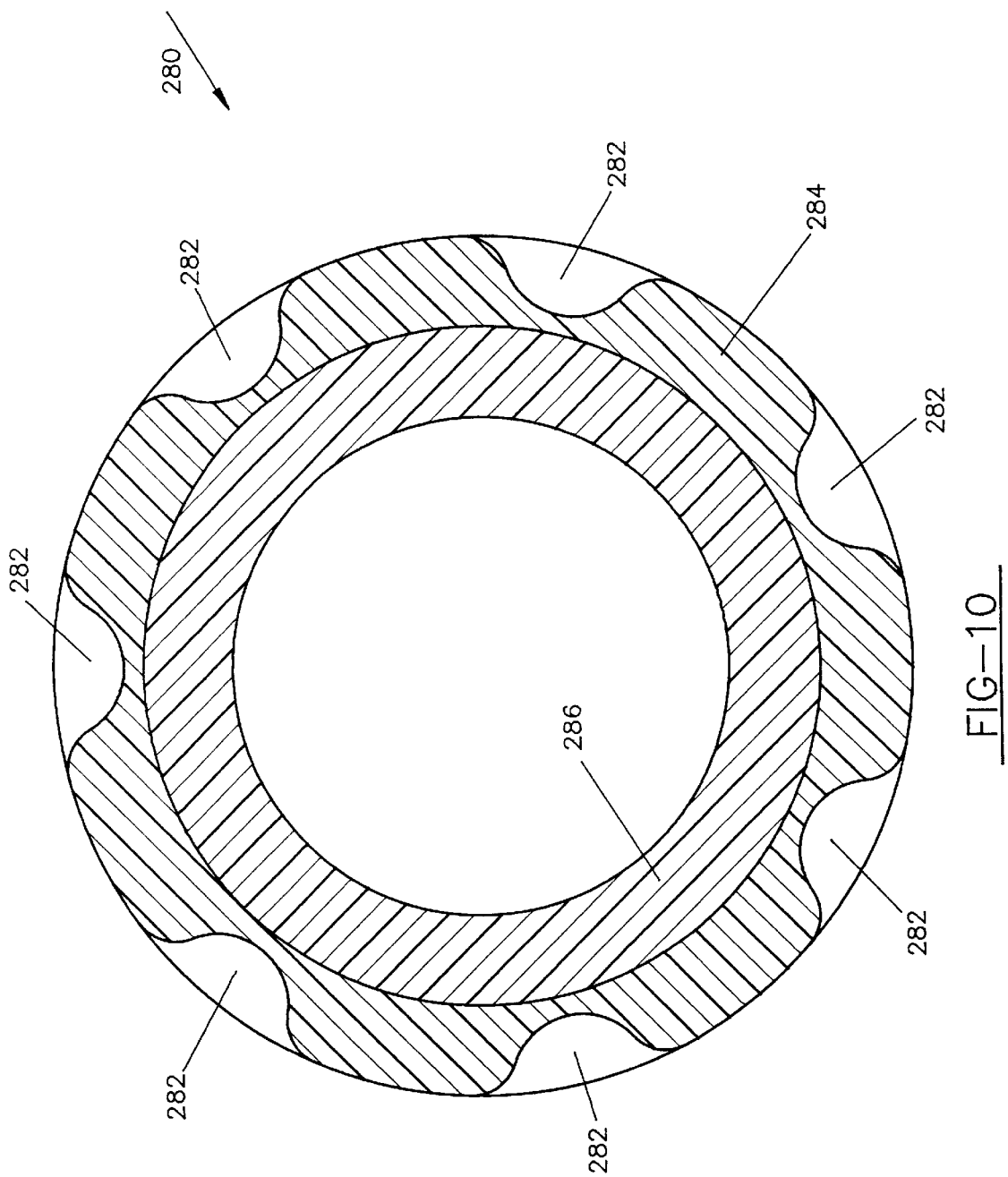
FIG. 10 shows an end view of still another modified suction tip of the present invention.
Figure 11:
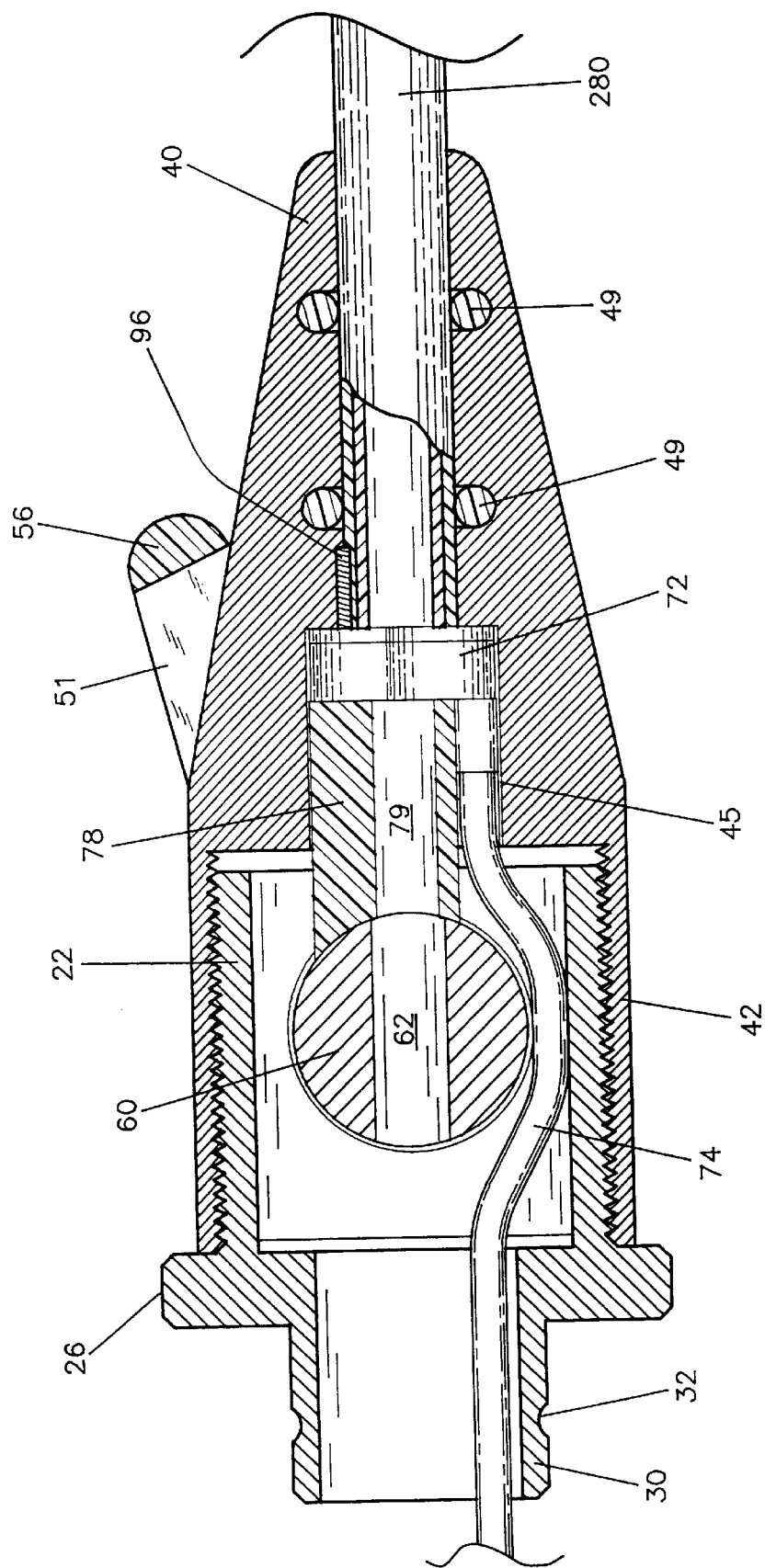
FIG. 11 is a cross sectional view of still another modified dental suction tool with the suction valve in the open position.

FIGS. 10 and 11 show still another modification of the dental suction tool 10 of the present invention. Like reference numerals are used to identify the elements from FIGS. 1–3 that are the same in FIG. 9 and FIG. 10.

The embodiment of the invention shown in FIG. 9 and FIG. 10 also use the key 96 that is added to the rear cavity 45 in front of the light ring 72. This key 96 will act as an alignment device when the suction tip 280 is inserted into the valve body 40.

The suction tip 280 also eliminates the fiberoptic layer on the inside of the suction tip. In this embodiment, the suction tip 280 is comprised of two extruded layers of plastic material, an outer layer 284 of opaque material and an inner layer 286 of clear plastic material that is light transmitting. The suction tip 280 has a plurality of recesses 282 that are positioned around the circumference of the suction tip 280 in equally spaced locations. When the light ring 72 is activated, light emitting therefrom will travel through the inner layer 284 of the suction tip 280 and be emitted from the end thereof. The outer layer 284 being opaque will prevent light loss through the lateral sides of the suction tip 280 so that the light intensity emitted from the end of the suction tip 280 is increased.

Figure 12:
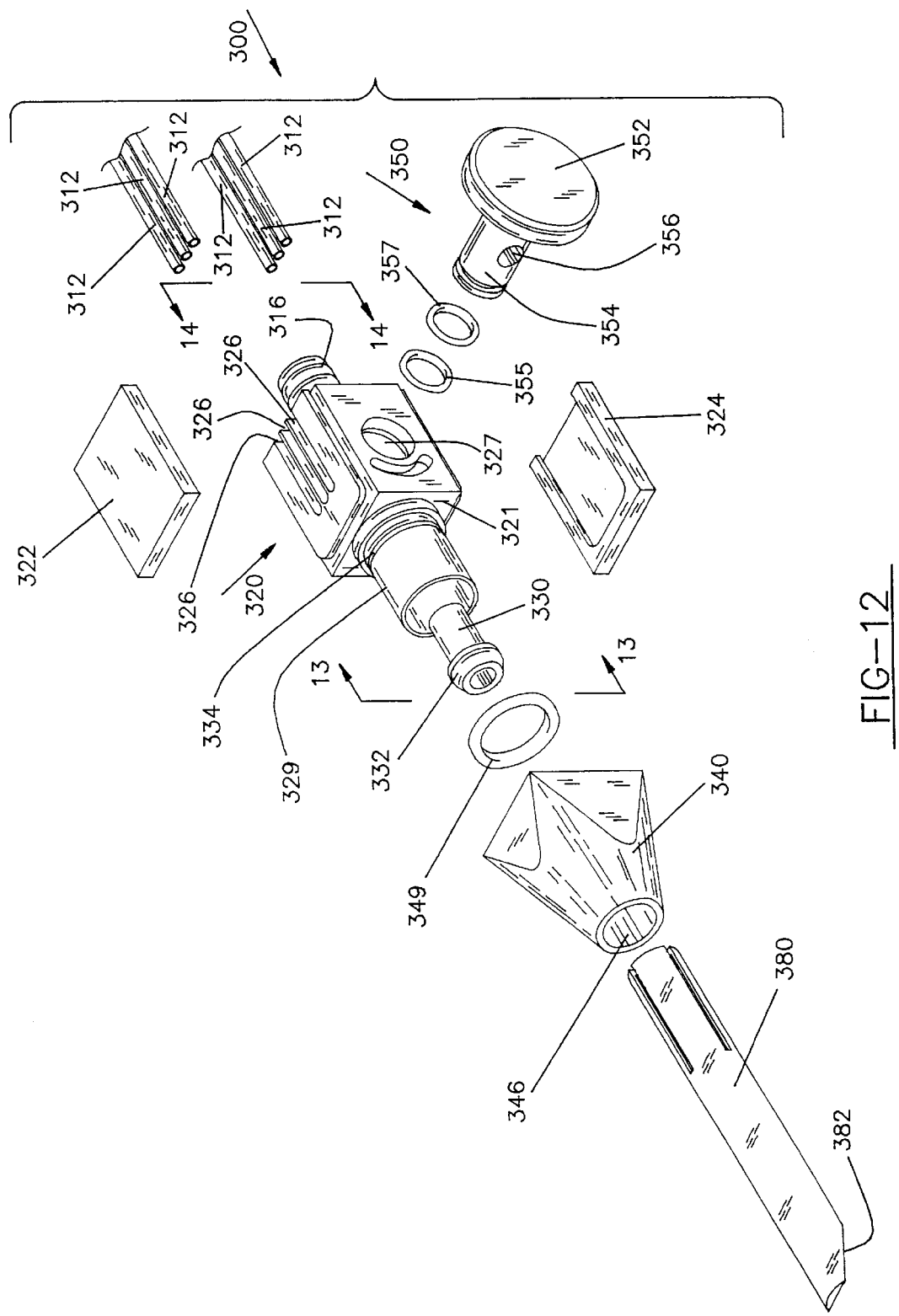
FIG. 12 is an isometric exploded view of another modified dental suction tool of the present invention.
Figure 14:
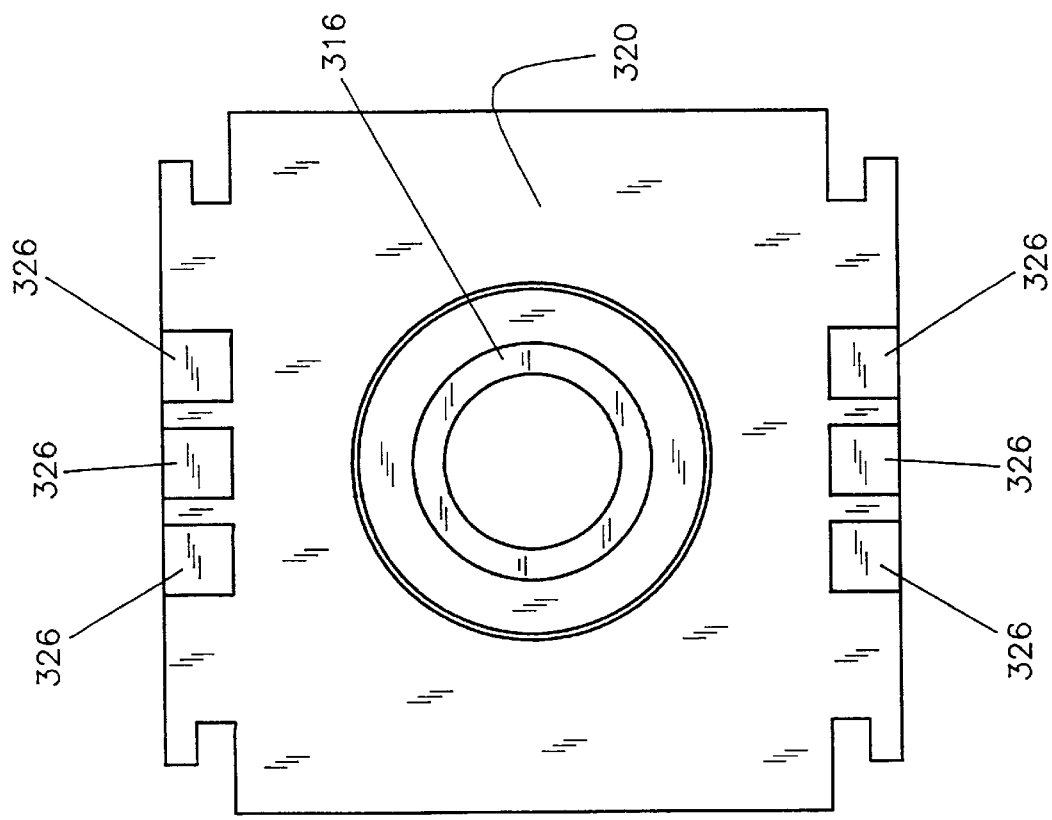
FIG. 14 is an end view of the valve body of the modified dental suction tool taken along line 14—14 of FIG. 12.
Figure 13:
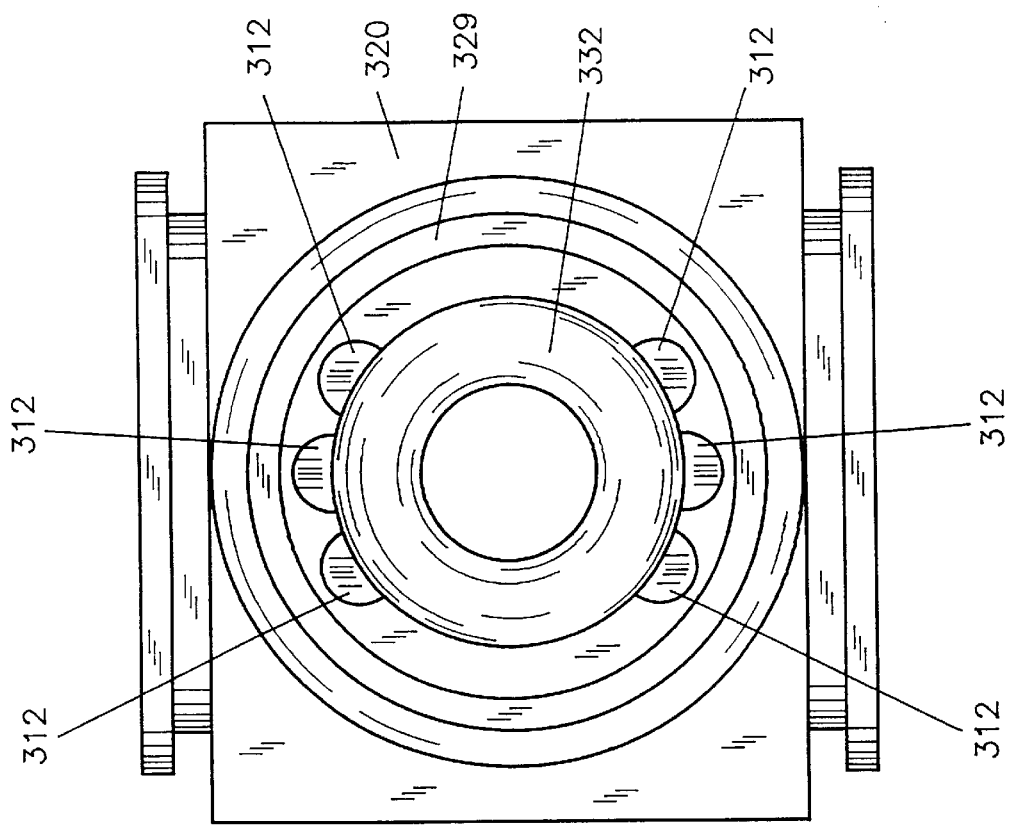
FIG. 13 is an end view of the valve body of the modified dental suction tool taken along line 13—13 of FIG. 12.

Another embodiment of the dental suction tool of the present invention is shown generally at 300 in FIG. 12. The dental suction tool 300 comprises a valve body 320, a tip holder 340, a rotating cylinder 350 and a plurality of fiberoptic bundles 312. A suction tip 380 is mounted in the tip holder 340 and the entire dental suction tool 300 is connected to a source of vacuum and electrical power (not shown).

The valve body 320 comprises a main section 321 including a suction line connector 316 integrally formed therewith. The main section 321 and the suction line connector 316 have a passageway 318 extending therethrough so that the source of vacuum can be provided to the suction tip 380. On the top of the main section 321 are a plurality of fiberoptic bundle channels 326 in which are seated the fiberoptic bundles 312 and a top valve body cover 322 is placed thereover by any suitable fastening means, such as the interlocking shoulder assembly shown in FIG. 15. The bottom of the main section 321 also has a plurality of fiberoptic bundle channels (not shown, but similar to channels 326) which also seat the fiberoptic bundles 312 and are covered by the bottom valve body cover 324 which is also held in place by any suitable fastening means, such as the interlocking shoulder assembly shown in FIG. 15. The fiberoptic bundles 312 extend through the main section 321 and terminate on the interior of the main section 321 at the point in which the main section 321 joins to the main section extension 329. This allows the light emitting from the end of the fiberoptic bundles 312 to interact with the end of the suction tip 380 as will be explained further herein. As an alternative to the use of fiberoptic bundles 312, any suitable light transmitting conduits may be used; as few as one light transmitting conduit can be used as long as the intensity of the light transmitted through the light transmitting conduit to the suction tip and from there into the patient's oral cavity is sufficient to provide the desired amount of illumination.

On each of the diametrically opposite sides of the valve body 320, an aperture 327 is provided of sufficient diameter to receive the rotating cylinder 350 therethrough when the dental suction tool 300 is assembled. The rotating cylinder 350 comprises a cylinder body 354 having a passageway 356 therethrough and the rotating cylinder 350 is held in place inside the valve body 320 by means of O ring 355 and O ring 357. The rotating cylinder 350 also has a cylinder cap 352 which can be gripped by the user to effect rotation of the rotating cylinder 350 to open and close the passageway 356 relative to the passageway 318 to control the suction provided to the suction tip 380.

At one end of the main section 321 there is a main section extension 329 that comprises a hollow cylindrical body. This main section extension 329 surrounds a bushing extension 330 which is press fit into a recess in the main section 321. The bushing extension 330 has a tip bushing 332 thereon. The tip bushing 332 preferably has a circumferential conical shape to receive the end of the suction tip 380 as will be explained herein. The bushing extension 330 also has an internal passageway 331 aligned with the passageway 318. At the approximate junction of the main section extension 330 with the main section 321, there is provided a groove 334 which receives an O ring 349.

Also provided is a tip holder 340 which is preferably a conically-shaped member. The wide end of the tip holder 340 has an interior circumferential shoulder 342 that cooperates with the O ring 349 to hold the tip holder 340 in place when it is assembled onto the valve body 320.

The tip holder 340 includes a suction tip passageway 348 which opens at the end of the tip holder 340 and in which is inserted the disposable suction tip 380.

Figure 17:
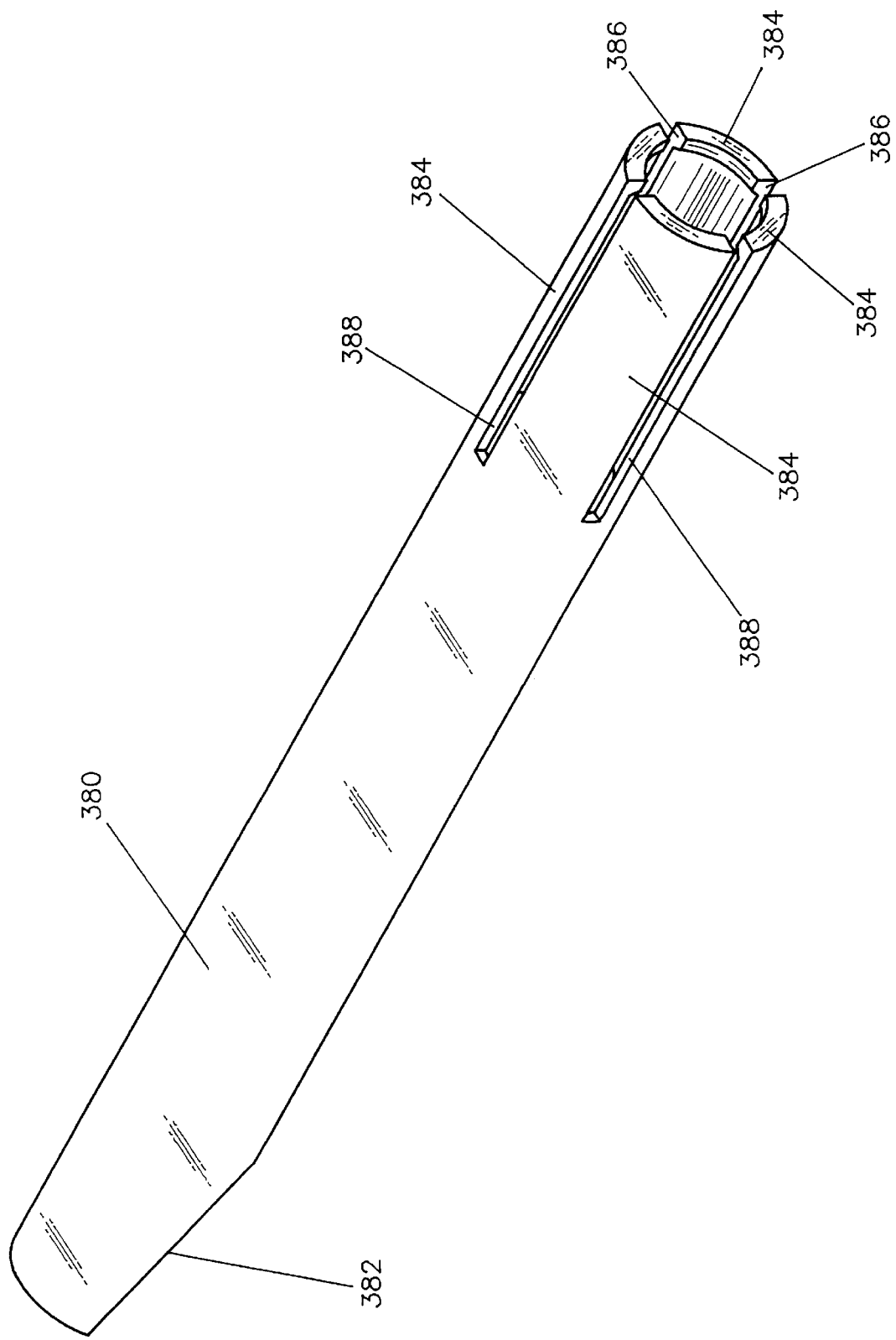
FIG. 17 is an isometric view of the suction tip used in the modified dental suction tool of FIG. 12.

The details of one of the preferred embodiments of the suction tip 380 are shown in FIG. 17. The suction tip 380 is a generally cylindrical hollow member having at one end a beveled section 382. At the opposite end of the suction tip 380, there are provided a plurality of fingers 384. In the preferred embodiment of the present invention, four slots 388 are shown equally spaced around the circumference of the suction tip 380. While the maximum depth of the slots 388 should not exceed the axial length of the tip holder 340 (in order to maintain the vacuum inside the suction tip 380), the minimum depth of the slots 388 should not be less than 0.125". The slots 388 create a plurality of fingers 384 at the end of the suction tip 380. The end of each finger 384 is provided with an interior shoulder 386 of the appropriate size to interact with the tip bushing 332 on the bushing extension 330.

Figure 15:
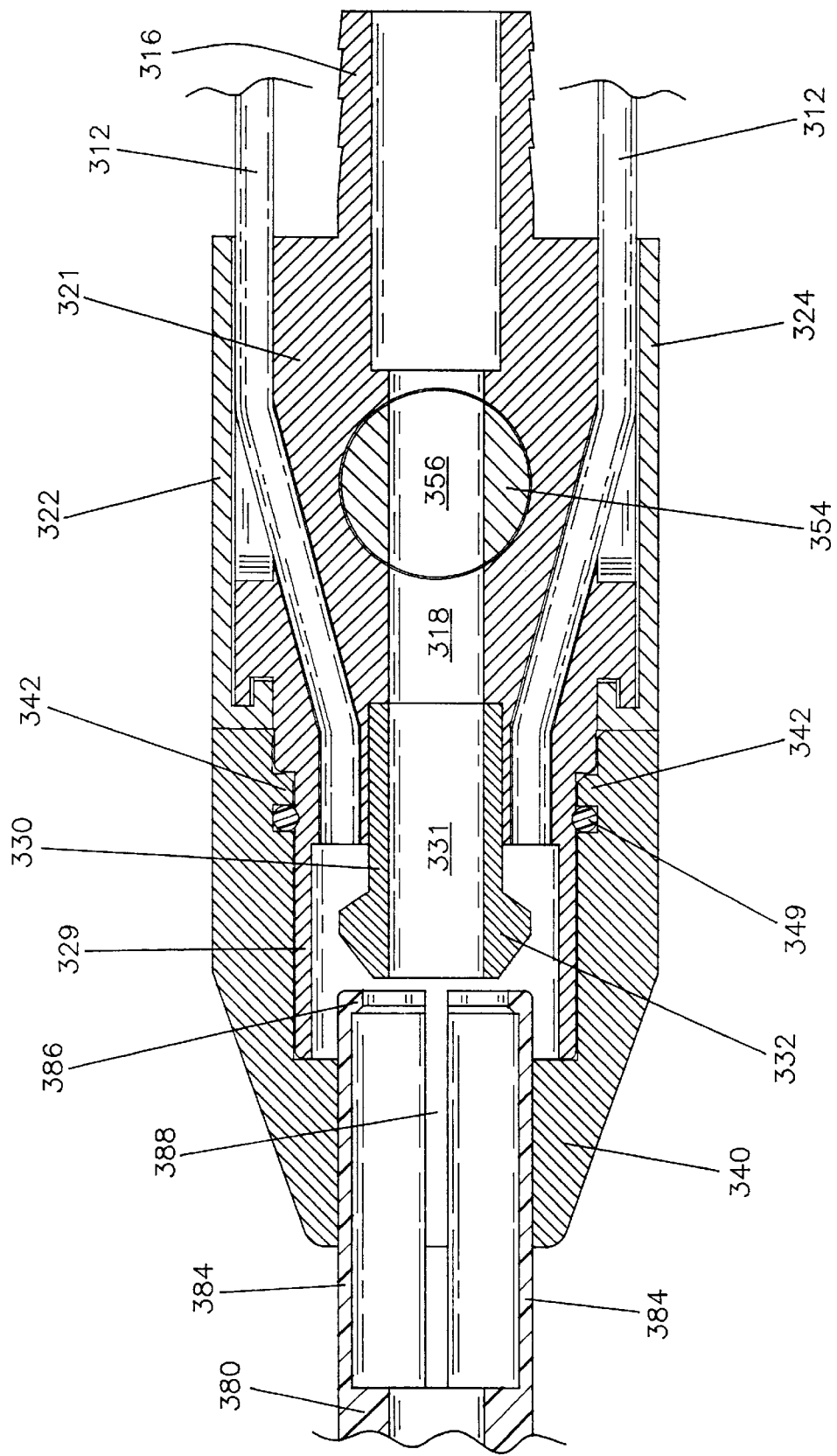
FIG. 15 is a cross section view of the modified dental suction tool of FIG. 12 before the suction tip is mounted onto the tip bushing.
Figure 16:
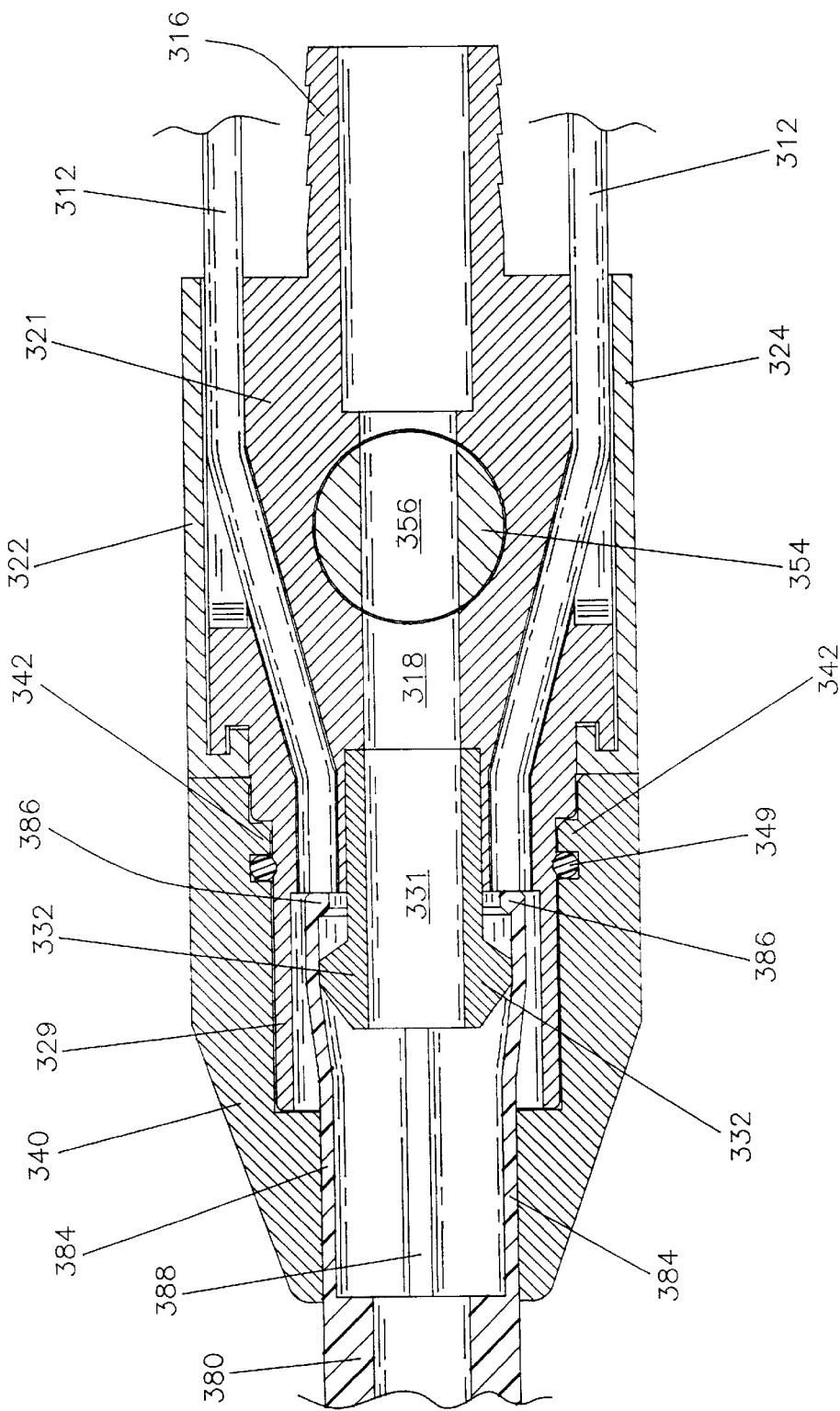
FIG. 16 is a cross section view of the modified dental suction tool of FIG. 12 with the suction tip mounted onto the tip bushing.

FIGS. 15 and 16 show the assembly of the dental suction tool 300. The O ring 349 is mounted into the groove 334. The tip holder 340 is positioned over the bushing extension 330 and is snapped into place by means of the shoulder 342 interacting with the O ring 349. The end of the suction tip 380 having the fingers 384 is inserted into the tip holder 340 and pushed therein until the fingers 384 spread out and hook over the tip bushing 332 on the bushing extension 330. The shoulders 386 on the interior of the fingers 384 interact with the tip bushing 332 to prevent the suction tip 380 from simply falling out of the tip holder 340, but the suction tip 380 is flexible enough to allow the suction tip 380 to be manually removed and replaced with a new suction tip 380 when needed.

When the suction tip 380 is inserted into the suction tip passageway 348 of the tip holder 340 and pushed onto the tip bushing 332, the end of the suction tip 380 is positioned adjacent the ends of the fiberoptic bundles 312 so that light emitting from the ends of the fiberoptic bundles 312 can be transmitted into the suction tip 380. By simply pulling out the suction tip 380, a new suction tip 380 can be inserted into the tip holder 340 for each new patient thereby maintaining a clean and sanitary suction tool and the elimination of any possible cross contamination between patients.

Activation of the power supply transmits light through the fiberoptic bundles 312. The light emitting from the fiberoptic bundles 312 is transmitted along the length of the suction tip 380 and out the end thereof into the patient's oral cavity.

Figure 18:
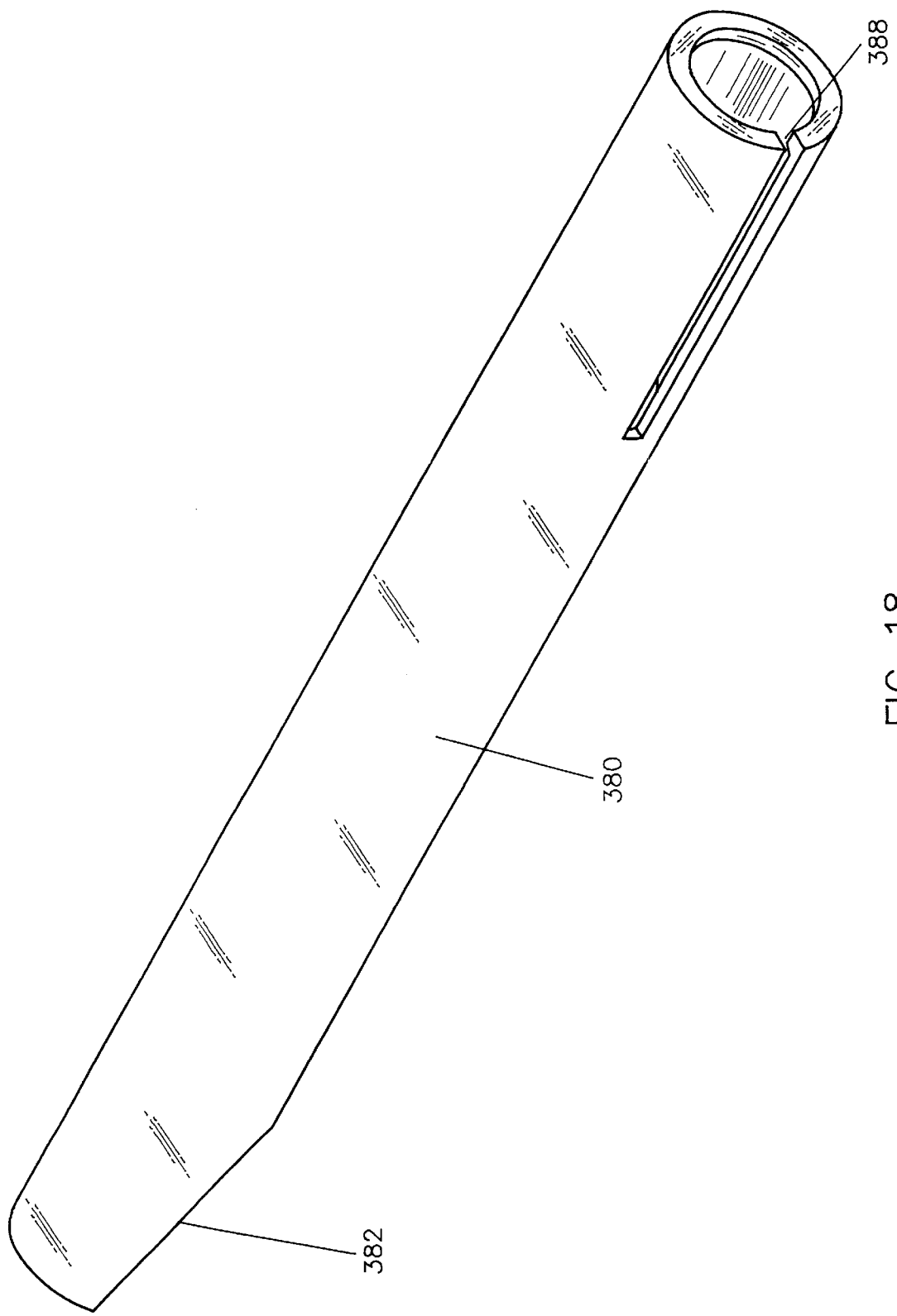
FIG. 18 is an isometric view of a modified suction tip used in the modified dental suction tool of FIG. 12.

Other modifications can be made to this embodiment. As shown in FIG. 18, the suction tip 380 can be made with a single slot 388 instead of the four slots 388 shown in FIG. 17. In this single slot 388 embodiment, there is still enough flexibility in the plastic material so that the open end of the suction tip 380 can expand around the tip bushing 332 and be held in place. As long as at least one slot 388 is used, the suction tip 380 is functional. More than one slot may also be used.

Figure 19:
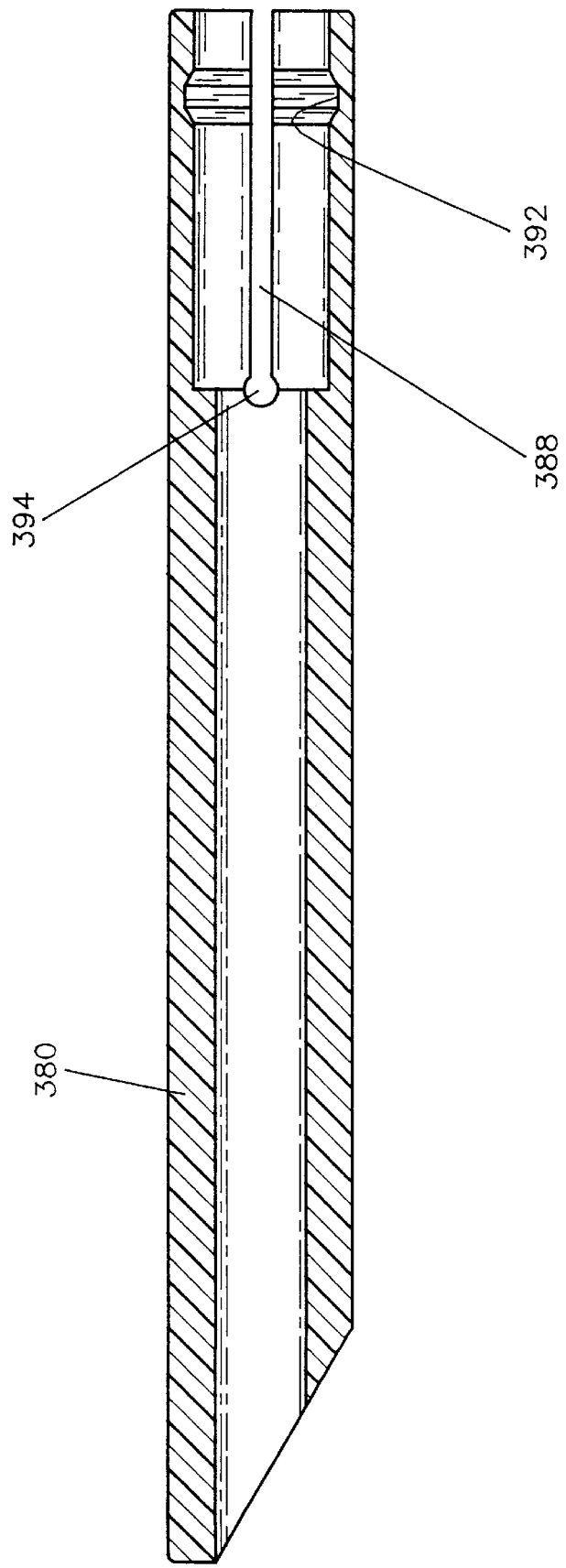
FIG. 19 is a cross sectional view of another modified suction tip used in the modified dental suction tool of FIG. 12.
Figure 20:
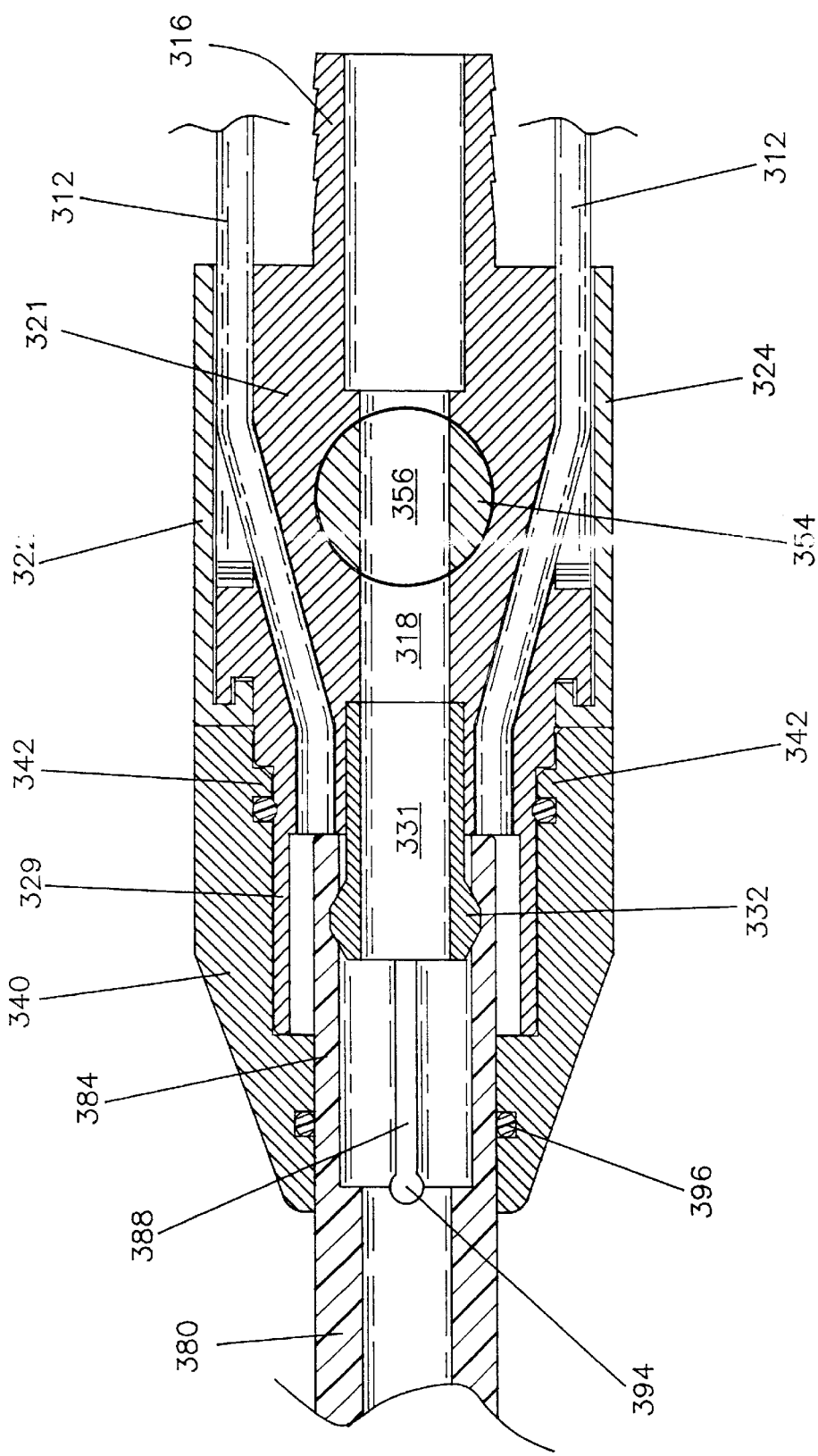
FIG. 20 is a cross sectional view of the modified suction tip of FIG. 19 used in the modified dental suction tool of FIG. 12.

FIGS. 19 and 20 show another modification of the suction tip 380 of the present invention. In this embodiment, the shoulder 386 is omitted and an internal groove 392 is used in its place. When the suction tip 380 is pushed onto the tip bushing 332, the tip bushing 332 sets into the internal groove 392 to hold the suction tip 380 in place. One or more slots 388 are required, such as the two diametrically opposed slots 388 shown in FIGS. 19 and 20. Additionally, a vacuum relief aperture 394 can be provided at the closed end of the slot 388. Also, to provide additional gripping pressure on the suction tip 380, an O ring 396 can be included in the tip holder 340.

In the preferred embodiment of this modification, a clear plastic material that is light transmitting is used for the suction tip 380. Suitable materials that can be used are acrylics, cellulosics and other light conducting plastics.

While the invention has been illustrated with respect to several specific embodiments thereof, these embodiments should be considered as illustrative rather than limiting. Various modifications and additions may be made and will be apparent to those skilled in the art. Accordingly, the invention should not be limited by the foregoing description, but rather should be defined only by the following claims.

What is claimed is:

1. A dental suction tool comprising:
   a) a valve body having a passageway therein for transmitting suction to a suction tip attached to the valve body, the valve body including a rotating cylinder therein for selectively providing suction to the valve body when a source of suction is attached to the valve body;

b) the suction tip made of material capable of transmitting light along the length of the suction tip;

c) a valve cap fastened to the valve body for securing the suction tip in the valve body;

d) at least one light transmitting conduit positioned on the interior of the valve cap adjacent an end of the suction tip so that when the light transmitting conduit is connected to a light source and the light source is activated, light is transmitted along the light transmitting conduit and into the suction tip and subsequently emitted from an end of the suction tip.

2. The dental suction tool of claim 1 wherein the suction tip comprises a clear plastic disposable material.

3. The dental suction tool of claim 1 wherein:

a) the valve body includes a tip bushing provided with a generally conical bushing extension and sized to receive a first end of the suction tip; and b) the suction tip comprises a hollow generally cylindrical hollow tubing with the first end thereof being provided with at least one axial slot so that the suction tip can be pushed over the tip bushing to secure the suction tip onto the valve body.

4. The dental suction tool of claim 3 wherein an interior shoulder is provided at the first end of the hollow tubing such that the interior shoulder can engage the bushing extension to secure the suction tip onto the valve body.

5. The dental suction tool of claim 1 wherein:

a) the valve body includes a tip bushing provided with a generally conical bushing extension and sized to receive a first end of the suction tip; and b) the suction tip comprises a hollow generally cylindrical hollow tubing with the first end thereof being provided with a plurality of axial slots forming a plurality of flexible fingers at the first end of the suction tip so that the suction tip can be pushed over the tip bushing to secure the suction tip onto the valve body.

6. The dental suction tool of claim 5 wherein an interior shoulder is provided on each finger at the first end of the hollow tubing such that the interior shoulder can engage the bushing extension to secure the suction tip onto the valve body.

7. The dental suction tool of claim 1 wherein:

a) the valve body includes a tip bushing provided with a generally conical bushing extension and sized to receive a first end of the suction tip; and b) the suction tip comprises a hollow generally cylindrical hollow tubing, an interior groove being provided adjacent the first end of the suction tip so that when the suction tip is pushed over the tip bushing the interior groove interacts with the bushing extension to secure the suction tip onto the valve body.

8. A disposable suction tip for use in a dental suction tool comprising a disposable, light transmitting plastic material capable of transmitting light along the length thereof and formed as a generally cylindrical hollow tubing, a first end of the suction tip having at least one axial slot therein so that the suction tip can be secured in the dental suction tool, the suction tip being made as a unitary piece.

9. The suction tip of claim 8 wherein an interior shoulder is provided at the first end of the hollow tubing such that the interior shoulder can engage a cooperative assembly in a valve body to secure the suction tip onto the valve body.

10. A disposable suction tip for use in a dental suction tool comprising a disposable, light transmitting plastic material capable of transmitting light along the length thereof and formed as a generally cylindrical hollow tubing, a first end of the suction tip having a plurality of axial slots therein forming a plurality of flexible fingers so that the suction tip can be secured in the dental suction tool, the suction tip being made as a unitary piece.

11. The suction tip of claim 10 wherein an interior shoulder is provided on each finger at the first end of the hollow tubing such that the interior shoulder can engage a cooperative assembly in a valve body to secure the suction tip onto the valve body.

12. A suction tip for use in a dental suction tool comprising a disposable plastic material capable of transmitting light along the length thereof and formed as a generally cylindrical hollow tubing, an interior groove being provided adjacent a first end of the suction tip, the suction tip further including at least one axial slot extending from the first end of the suction tip along a portion of the axial length of the suction tip so that the suction tip can be secured in the dental suction tool.

13. The suction tip of claim 12 wherein a vacuum relief aperture is provided at a closed end of the axial slot.

14. The suction tip of claim 12 wherein two diametrically opposed axial slots are provided.

15. The suction tip of claim 14 wherein a vacuum relief aperture is provided at a closed end of each of the axial slots.

16. A dental suction tool comprising:

a) a valve body including a rotating cylinder therein attached to a lever for selectively providing suction to the valve body;

b) a suction tip capable of transmitting light mounted in the valve body;

c) a valve cap fastened to the valve body, the valve cap having a generally hollow interior;

d) a light assembly positioned on the interior of the valve cap adjacent an end of the suction tip so that when the light assembly is activated, light is transmitted along the suction tip and emitted from an end thereof.

17. The dental suction tool of claim 16 wherein the suction tip comprises a clear plastic disposable material.

18. The dental suction tool of claim 16 wherein the suction tip comprises an outer layer of material opaque to light and an inner layer of clear plastic material capable of transmitting light.

19. The dental suction tool of claim 16 wherein the suction tip comprises an outer layer of plastic material and an inner layer of fiberoptic material capable of transmitting light.

20. The dental suction tool of claim 16 further comprising at least one beveled section on an end of the suction tip and a tip insertion block positioned on the interior of the valve body, the tip insertion block having an interior configuration complementary to the beveled section of the suction tip so that the suction tip is properly aligned in the valve body when inserted therein.

21. The dental suction tool of claim 16 further comprising at least one recess on an end of the suction tip and a key positioned on the interior of the valve body, the key having a configuration complementary to the recess on the suction tip so that the suction tip is properly aligned in the valve body when inserted therein.

22. The dental suction tool of claim 21 wherein a plurality of recesses are positioned around a circumference of the suction tip so that the suction tip may be positioned in association with the key in a plurality of axial positions.

* * * * *